United States Patent
Jacobus et al.

(10) Patent No.: US 6,551,614 B2
(45) Date of Patent: Apr. 22, 2003

(54) ANTIMALARIAL N,N'-SUBSTITUTED BIGUANIDES DERIVED FROM HYDROXYLAMINES

(75) Inventors: David P. Jacobus, Princeton, NJ (US); Norman P. Jensen, Princeton, NJ (US)

(73) Assignee: Jacobus Pharmaceutical Co., Inc., Princeton, NJ (US)

( * ) Notice: Subject to any disclaimer, the term of this patent is extended or adjusted under 35 U.S.C. 154(b) by 0 days.

(21) Appl. No.: 09/805,635

(22) Filed: Mar. 14, 2001

(65) Prior Publication Data

US 2003/0040544 A1 Feb. 27, 2003

(51) Int. Cl.⁷ .................................................. H61K 9/48
(52) U.S. Cl. ........................ 424/451; 424/400; 424/464; 424/422; 514/633; 514/331; 514/616; 514/660
(58) Field of Search ................................. 514/635, 331, 514/616, 630; 424/400, 457, 464, 422

(56) References Cited

U.S. PATENT DOCUMENTS

| | | | |
|---|---|---|---|
| 3,660,394 A | 5/1972 | Mamalis | 260/249.9 |
| 5,322,858 A | 6/1994 | Canfield et al. | 514/635 |

FOREIGN PATENT DOCUMENTS

| | | |
|---|---|---|
| DE | 1957769 | 9/1970 |
| GB | 1250531 | 10/1971 |

OTHER PUBLICATIONS

Mamalis et al., "Amino–oxy–derivatives, etc.", J. Chem. Soc. (1962) pp. 3915–3926.

Primary Examiner—Thurman K. Page
Assistant Examiner—Lakshmi Channavajjala
(74) Attorney, Agent, or Firm—Woodcock Washburn LLP

(57) ABSTRACT

Compounds of the formulae

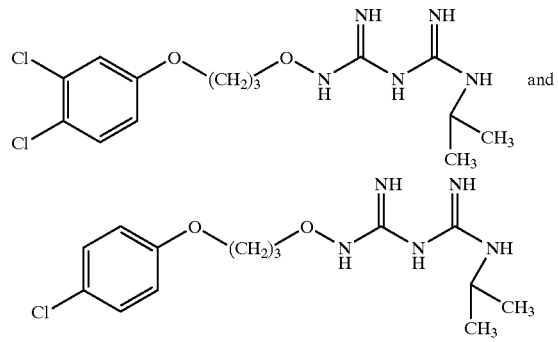

are disclosed. A method of protecting subjects from infections caused by an organism of the group: Plasmodium sp., Mycobacterium sp., *P. falciparum, M. avium* complex, *M. tuberculosis, M. kanasii* and *Pneumocystis carinii* by administering to the subjects liable to infections, a prophylactically effective amount of a compound of the foregoing formulae; and a method of reducing the level of infection in subjects caused by the above-listed organism by administering to the subjects an infection reductively effective amount of a compound of the foregoing formulae are also disclosed.

8 Claims, No Drawings

ANTIMALARIAL N,N'-SUBSTITUTED BIGUANIDES DERIVED FROM HYDROXYLAMINES

BACKGROUND OF THE INVENTION

1. Field of the Invention

This invention relates to N,N'-substituted asymmetrical imidodicarbonimidic diamides derived from hydroxylamines and their derivatives, to a process for making them, to a pharmaceutical composition thereof and a method for protecting and/or treating a mammalian subject from infections caused by an organism selected from the group consisting of Plasmodium sp., Mycobacterium sp. and *Pneumocystis carinii*.

2. Reported Developments

Malaria is an infectious febrile disease caused by protozoa of the genus Plasmodium, which are parasitic in the red blood cells, and are transmitted by the bites of infected mosquitoes of the genus Anopheles. The disease is characterized by attacks of chills, fever, and sweating, occurring at intervals which depend on the time required for development of a new generation of parasites in the body. After recovery from the acute attack, the disease has a tendency to become chronic, with occasional relapses. Among the various forms of malaria falciparum or pernicious malaria is the most serious form of malaria caused by *Plasmodium falciparum*, characterized by severe constitutional symptoms and sometimes causing death. The disease is prevalent in tropical and subtropical areas of the world including the Amazon region of Brazil, East and Southern Africa and Southeast Asia. Malaria has been treated with various drugs throughout recent history including combinations of drugs. While marginally successful against some strains of malaria, most strains of malaria appear to have developed resistance not only to individual drugs but also to multiple combinations of drugs. Multiple Drug Resistance, hereinafter sometimes referred to as MDR, continues to confound antimalarial drug development efforts. Drugs of diverse chemical classes, such as mefloquine, halofantrine, and artemisinin, appear to be expelled by a common transport or efflux mechanism. The mechanism of resistance to the classic antifolate antimalarials is independent of drug transport or efflux and is due to differential binding affinities to parasite dihydrofolate reductase, hereinafter sometimes referred to as DHFR, and or dihyropteroate synthase, hereafter sometimes referred to as DHPS. Efforts have been and are being made to develop DHFR inhibitors in combination with DHPS inhibitors. The efforts so far have resulted in limited success.

U.S. Pat. No. 5,322,858 to Canfield et al., which is incorporated herein by reference in its entirety, discloses N,N'substituted imidocarbonimidic diamides derived from hydroxylamines, pharmaceutical formulations thereof, and methods of protecting subjects from Plasmodium sp., Mycobacterium sp. and *Pneumocystis carinii* by administering to a subject liable to such infection a prophylactically effective amount of said pharmaceutical formulations. The formulations are said to reduce the level of infection where said subjects have already been infected.

The patent discloses a large number of compounds in generic formula 1:

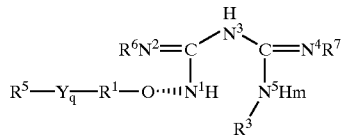

wherein:

wherein $R^1$ is a substituted or unsubstituted divalent aliphatic group of 1 to 16 carbon atoms; wherein the substituents are mono or poly and are selected from the group consisting of lower alkyl, aryl and arlkyl, $R^3$ is selected from the group consisting of the same group of values as $R^5$ other than carbocycloaryl, and when further bonded to the nitrogen to which it is attached, a saturated heterocycle of 4–8 carbon atoms, $R^5$ is selected from the group consisting of substituted and unsubstituted alkyl of 1–10 carbon atoms, aryl, cycloalkyl and heterocycloalkyl of 3–8 carbon atoms, mono or polycarbocycloaryl of 4–7 atoms per ring, wherein the substituents are; mono or poly and are selected from the group consisting of lower alkyl, cycloalkyl of 3–8 carbon atoms, lower alkenyl, lower alkynyl, nitro, lower alkoxy, lower alkoxycarbonyl, phenyl loweralkyl, phenyl, mono and polyhalophenyl, phenoxy, mono and polyhalophenoxy, and halo provided however, that such halo substitution is in a mono and polycarbocycloaryl of 4–7 atoms per ring. $R^6$ and $R^7$ which may be the same or different are hydrogen alkanoyl or alkoxy alkanoyl, and when further bonded to the nitrogen to which either is attached, a saturated heterocycle of 4–8 carbon atoms, and $R^7$ may also be selected from the group consisting of same group of values as $R^5$, and when further bonded to the nitrogen to which it is attached, a saturated or unsaturated heterocycle of 4–8 carbon atoms, Y is oxygen or sulfur, q is 0 or 1, n m is 1 or 0, having the latter value where $R^3$ is a moiety having two bonds attached to $N^5$, provided that unless otherwise stated the prefix alk designates moieties which are straight chain or branched chain of 1–24 carbon atoms, and when further prefixed by the term lower, designates 1–6 carbon atoms, the respective tautomers thereof, the pharmaceutically acceptable salts and addition salts thereof and the hydrates of said salts and addition salts and mono and diacyl derivatives thereof.

In testing the compounds disclosed in the patent for antimalarial activity, one candidate, identified as WR250417 or PS15, hereinafter sometimes referred to as PS15, was demonstrated to have significant activity against drug-resistant *Plasmodium falciparum* as described by Canfield et al. 1993. PS-15: A potent, orally active antimalarial from a new class of folic acid antagonists. Am J. Trop Med Hyg 49: 121–126. The compound, N[3-(2,4,5-trichlorophenoxy)propyloxy]-N'-(1-methylethyl)imidodicarbonimidediamide hydrochloride has the structure:

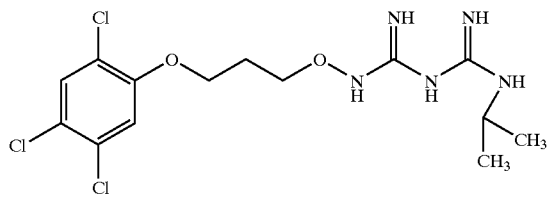

WR250417 or PS-15

The compound was found to be not cross-resistant with other inhibitors of DHFR, such as pyrimethamine and cycloguanil.

While PS-15 is similar in chemical structure to the well-known antimalarial drug Proguanil,

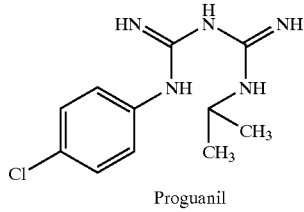

Proguanil it was envisioned to present a new series of antifolate drugs which were named hydroxylamine-derived biguanides. PS-15 displayed modest intrinsic antimalarial activity alone and was metabolized in vivo to WR99210, the extremely active triazine inhibitor of DHFR having the chemical structure

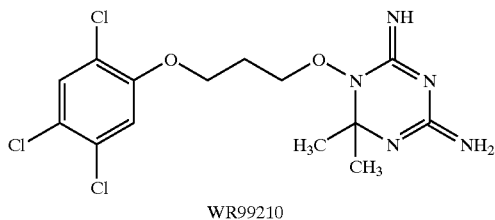

WR99210

When tested in vitro against drug-resistant clones of *P. falciparum*, it was found to be more active than proguanil, and the putative metabolite WR99210, and was found to be ten thousand times more active than the proquanil metabolite cycloguanil. PS-15 is also more active as well as less toxic than proguanil when administered orally to mice infected with *P. berghei*. When administered orally to Aotus monkeys infected with multidrug-resistant *P. falciparum*, the drug is more active than either proquanil or WR99210. Because PS15 had intrinsic antimalarial activity, and is not cross-resistant with other DHFR inhibitors, and could be metabolized to WR99210 in vivo, oral administration of this drug was predicted to circumvent the shortcomings and retain advantages found with both proguanil and WR99210. However, development of PS-15 was stifled by environmental regulatory compliance issues which prohibited the use of required starting material, 2,4,5-trichlorophenol in bulk drug manufacturing. The synthesis of PS-15 is shown in EXAMPLE 1, U.S. Pat. No. 5,322,858.

Numerous analogs of PS-15 were prepared and several were found to have equivalent antimalarial activity. A 90-day comparative toxicity experiment showed that, with the exception of PS-26 and PS-33, PS-15 and its analogs caused testicular toxicity.

SUMMARY OF THE INVENTION

We have now synthesized a series of N,N'-substituted biguanides and, unexpectedly, two of this series of N,N'-subsitituted biguanides were found to be free of testicular atrophy found with the other compounds in the series. The compounds are: 1-[3-(3,4-dichlorophenoxy)propyloxy]-5-isopropylbiguanide(hemisuccinate), hereinafter sometimes designated as PS-26

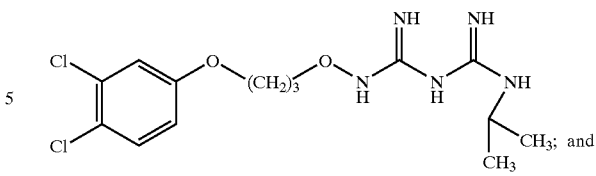

1-[3-(4-chlorophenoxy)propyloxy]-5-isopropylbiguanide (hemisuccinate), hereinafter sometimes designated as PS-33

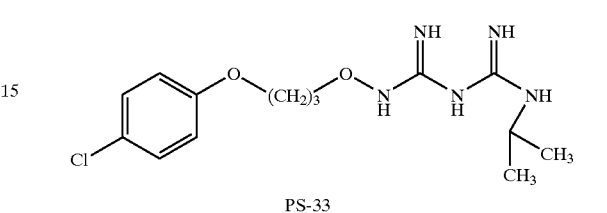

PS-33

The compounds of the present invention are formulated with a pharmaceutically acceptable carrier for oral or injectable administration.

Oral formulations are preferred and this invention has the advantage over related products of being readily absorbed by mammals in sufficient levels to make the compounds of the present invention orally active as therapeutic agents. Formulations for oral or injected use are based on sufficient solubility as to allow the therapeutic agent to enter solution in the stomach or in an injectable medium. The drug formulations will include tablets, pills, capsules, sachets, granules, powders, chewing gums, suspensions, emulsions and solutions: particularly preferred for oral use are tablets and capsules of all varieties and microbe-free solutions for injection or infusion. Where appropriate and necessary the formulations may include diluents, binding agents, dispersing agents, surface-active agents, lubricating agents, coating materials, flavoring agents, coloring agents, controlled release formulations, sweeteners or any other pharmaceutically acceptable additives, for example, gelatin, sodium starch glycolate, lactose, starch, talc, magnesium stearate, microcrystalline cellulose, Povidone, hydrogenated or unsaturated oils, polyglocols, syrups or other aqueous solutions. Where the formulations are tablets or capsules and the like the formulations may be presented as premeasured unit doses or in multidose containers from which the appropriate unit dose may be withdrawn.

The injectable form may be an aqueous or nonaqueous solution, suspension or emulsion in a pharmaceutically acceptable liquid, e.g. sterile pyrogen-free water or parenterally acceptable oils or mixture of liquids which may contain bacteriostatic agents, antioxidants or other preservatives and stabilizers, buffers (preferably but not limited to a physiological pH range of 6.5–7.7), solutes to render the solution isotonic with the blood, thickening agents, suspending agents or pharmaceutically acceptable additives. Such forms will be presented in unit dose form such as ampules or dispersable injection devices or in multi-dose forms such as a bottle from which the appropriate dose may be withdrawn, or as a solid form or concentrate which can be used to quickly prepare an injectable formulation. All formulations for injection are preferable sterile and pyrogen free. Suppositories containing the compound will also contain suitable carriers, e.g. cocoa butter, polyglycols or other state-of-the-art carriers.

In addition to standard pharmaceutical additives there may be included within formulations of the compound other therapeutic agents, particularly including other antimalarials and antiinfectives.

The preferred dosage range is between 0.5 and 10 mg/kg/day. The range is quite large because the physician must use his judgement on whether the dosage is prophylactic and if given to an infected subject, on what the level of infection is. When given as tablets the tablets may contain 25–250 mg of active material.

DETAILED DESCRIPTION OF THE INVENTION

We have surprisingly discovered that the compounds 1-[3-(3,4-dichlorophenoxy)propyloxy]-5-isopropylbiguanide(hemisuccinate), and 1-[3-(4-chlorophenoxy)propyloxy]-5-isoproplbiguanide (hemisuccinate), have excellent antimalarial activity against infections caused by an organism selected from the group consisting of Plasmodium sp., Mycobacterium sp. and *Pneumosistis carini* and do not show the testicular toxicity seen with the other analogs in the series.

These compounds can be prepared by using the following general synthetic schemes for biquanides.

neutralize; (e)sodium dicyanamide, HCl, alcoholic solvent, heat; (f) EtOAc, heat; (g) HCl, MeOH, (h)RT, DMF. Preparative methods for the compounds are described in EXAMPLES I AND II.

EXAMPLE I

PS-26: 1-[3-(3,4-dichlorophenoxy)propyloxy]-5-isopropylbiguanide hemisuccinate
3-(3,4-Dichlorophenoxy)propyl bromide A mixture of 3,4dichlorophenol (499.4 g. 3.06 moles), 1,3-dibromopropane (2424 ml, 12 moles), 24% sodium hydroxide (613 g, 3,83 moles), and 5 g of tetrabutylammonium hydrogen sulfate were stirred and heated at 50–70° C. for 2 h. The temperature was raised to 80° and heating was continued for 16 hr more. After cooling the lower phase was separated and excess dibromopropane was removed on a rotary evaporator. The residue was distilled through a short vigreux column at 1 mm vacuum. A total of 870 g (87.3%) of product was collected at 125–135° C. $^1$H-NMR (CDCl$_3$) & 2.23 (m, 2H), 3.50 (t, 2H), 4.02 (t, 2H), 6.7–7.2 (m, 4H).
3-(3,4-Dichlorophenoxy)propyloxyamine hydrochloride To a solution of 0.363 kg (3.3 moles) of potassium acetohydroxamate hydrate in 1.03 kg of 2-methoxyethanol

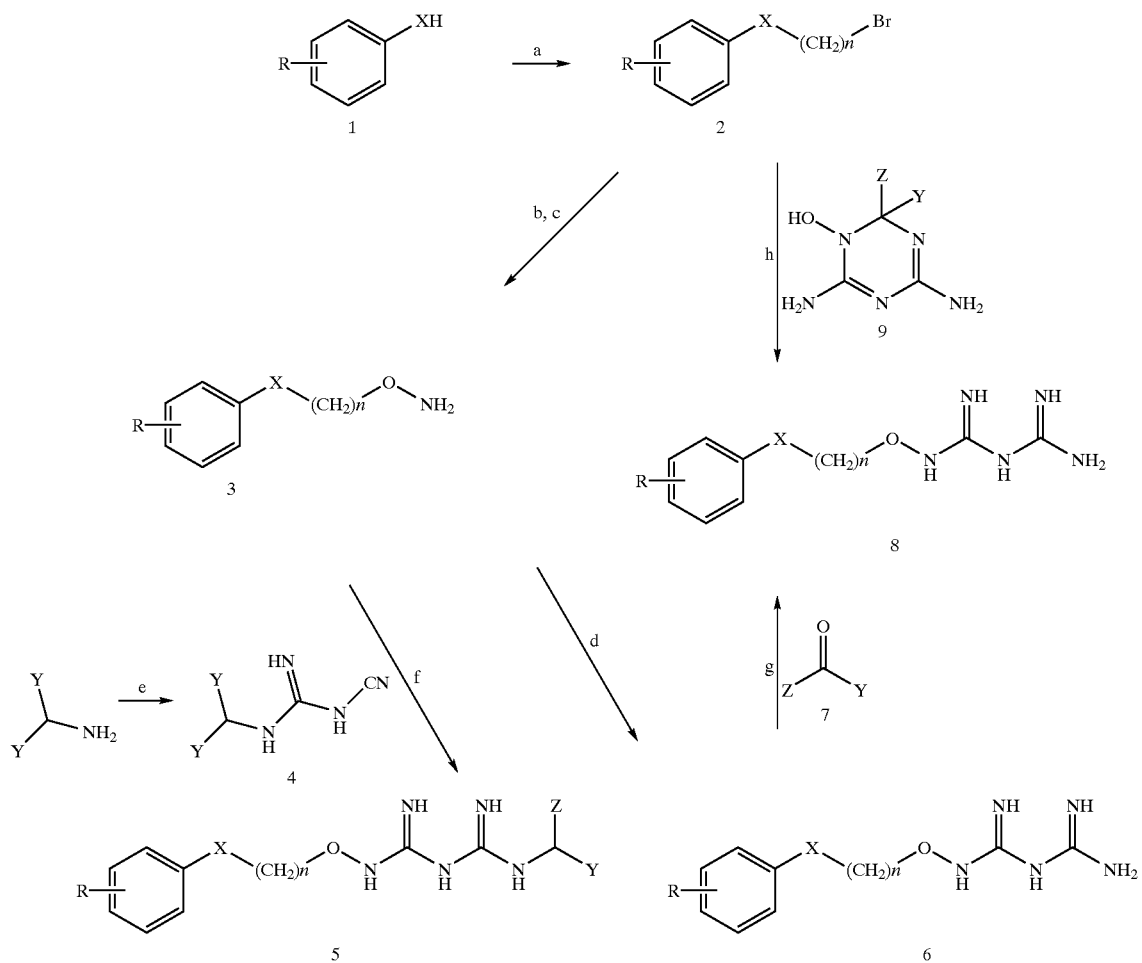

Reagents: (a), 1,3-dibromopropane(for n=3), NaOH, tetrabutylammonium hydrogen sulfate; (b) AcNHOH, NaOH or KOH; alcoholic solvent (c)conc. HCl, MeOH; (d)dicyandiamide, aq. EtOH, heat and then aqeous NaOH to solution was added 759 g (2.67 moles) of 3-(3,4-dichlorophenoxy)propyl bormide. The reaction mixutre was heated 2 hours at 55° C. After at exotherm to 70° C. the mixture was heated at 55° C. for an additional 16 hours.

After cooling to room temperature the KBr was removed by filtration. The filtrate containing crude 3-(3,4-dichlorophenoxy)propyl acetohydroxamate was stirred and 300 mL of conc. HCl (3.62 moles) was added. After 15 hr at room temperature the starting material was consumed. The mixture was concentrated in vacuo to give 810 g of crude product which was used without further purification.

1-[3-(3,4-Dichlorophenoxy)propyloxy]-5-isopropylbiguanide

A mixture of 765 g (2.8 moles) of the crude 3-(3,4-dichlorophenoxy)-propyloxyamine hydrochloride, 302 g (2.4 moles) of isopropyldicyandiamide[1] and 3.5 L of EtOAc was stirred and heated at 55° C. for 8 hr. After cooling insolubles were removed by filtration. The filtrate was stirred with 480 g (3.5 moles) of 24% NaOH. The organic layer was separated and dried with anhydrous $K_2CO_3$, decanted and dried with another portion of anhydrous $K_2CO_3$ before concentrating in vacuo to 1024 g of solid. Recrystallization for 1250 mL of ethanol gave 500 g which was recrystallized a second time from 1.0 L of ethanol to give the product mp 107–108° C. IR 3474, 3363, 3299, 3106, 1630, 1563 cm$^{-1}$; $^1$H-NMR (DMSO-d$_6$) δ1.06 (d, 6H), 2.0 (m, 2H), 3.7–4.2, (m, 5H), 4.85 (br s, 2H), 6.0 (br s, 1H), 6.5–7.5 (br s, 4H).

1-[3-(3,4-Dichlorophenoxy)propyloxy]-5-isopropylbiguanide hemisuccinate

A mixture of 453.6 g (1.252 moles) of 1-[3-(3,4-Dichlorophenoxy)propyloxy]-5-isopropylbiguanide, 1.0 L of ethanol and 74.4 g (0.630 moles) of succinic acid was heated to 60° C. to obtain a solution. A total of 500 ml of water was added dropwise at 60° C. After standing at room temperature for 15 hr the product was collected, washed with 300 mL of 50% ethanol cooled to 5° C. and dried at 105° C. for 3 hr to give 508 g (96.3%) mp 148.0–149.5°, $^1$H-NMR (DMSO-d$_6$) δ1.00 (d,. 6H), 1.9 (m, 2H) 2.20 (s, 2H), 3.5–4.2, (m, 5H), 5.5 (br s, 2H), 6.77.5 (m, 4H), 8.1 (br s, 4H).

EXAMPLE II

PS33: 1-[3-(4-chlorophenoxy)propyloxy]-5-isoproplbiguanide hemisuccinate 3-(4-Chlorophenoxy)propyl bromide A mixture of 4-chloropenol (998 g, 7.76 moles), 1,3-dibromoporpane (2500 ml, 24, 6 moles), 22% sodium hydroxide (1250 ml, 8.5 moles), and 10 g of tetrabutylammonium hydrogen sulfate were stirred and heated at 50–55° C. for 15 h. The temperature was raised to 80° C., an additional 50 mL of 22% sodium hydroxide was added, and heating was continued for 16 hr more at which time a TLC (eluant of hexane: ethyl acetate 5:1 with visualization by spraying with p-nitrophenydiazonium chloride spray of the reaction solution) indicated that the starting phenol was almost entirely consumed. After cooling the lower phase was separated and excess dibromopropane was removed on a rotary evaporator. The residue was distilled through a short Vigreux column at 1 mm vacuum. A total of 1655 g (84.5%) of product was collected at 112–118° C. $^1$H-NMR (CDCl$_3$) δ2.22(m, 2H), 3.44 (t, 2H), 4.01 (t, 2H), 6.7–7.3 (m, 4H).

3-(4Chlorophenoxy)propyloxyamine hydrochloride

To a solution of 0.91 kg (8.0 moles) of potassium acetohydroxamate hydrate in 4.96 kg of 2-methoxyethanol solution was added 1650 g (6.62 moles) of 3-(4-chlorophenoxy)propyl bromide. An additional 200 mL of 2-methoxyethanol was added and the reaction mixture was heated 2 hours at 50° C. After cooling to room temperature the KBr was removed by filtration and washed with 100 mL of 2-methoxyethanol. The filtrate and washings were concentrated on a rotovap, diluted with 1.0 L of EtOAc, and washed with a 600 mL and a 400 mL portion of water before concentration at high vacuum to yield 1707 g of crude 3-(4chlorophenoxy)propyl acetohydroxamate which was used without further purification. This crude material was dissolved in 5.0 L of methanol and 640 g of conc. HCl was added. After 15 hr the starting material was consumed, as determined by TLC utilizing the diazonium spray. The mixture was concentrated at oil pump vacuum to give 1537 g of crude product which was used without further purification. A sample recrystallized from EtOAc melted 115–116° C.

1-[3-(4-Chlorophenoxy)propyloxy]-5-isopropylbiguanide

A mixture of 754 g (3.17 moles) of crude 3-(4-Chlorophenoxy)-propyloxyamine hydrochloride, 398 g (3.16 moles) of isopropyldicyandiamide[1] and 4.0 L of EtOAc was stirred and heated at 50° C. for 15 hr. After 1 and 3 hours of heating additional 20 and 10 g portions of isopropyldicyandiamide were added. After cooling 18 g of 1,5-bis(isopropyl)biguanide which was present in the isopropyldicyandiamide starting material was removed by filtration. The filtrate was stirred with 260 g (3.25 moles) of 50% NaOH and 130 g of $K_2CO_3 \cdot 1.5H_2O$ in 1.0 L water. The organic layer was separated and stirred with 100 g of anhydrous $K_2CO_3$ and then 90 g of $MgSO_4$ before concentrating in vacuo to 1013.5 g of solid. Recrystallization for 2.0 L of ethanol gave 625 g of product mp 98–100° C. IR 3467, 3352, 3321, 1635, 1606, 1563 cm$^{-1}$; $^1$H-NMR (DMSO-d$_6$) δ1.03 (d, 6H), 2.0 (m, 2H), 3.75–4.10 (m, 5H), 4.83 (br s, 2H), 6.0 (br s, 1H), 6.6(br s, 2H), 6.8–7.3(m, 4H) ≠$^1$Crud, F.H.S.; Hendry, J. A.; Kenny, T. S.; Murray, A. G.; Rose, F. L. Synthetic Antimaterials, Part XXVII. An Alternative Route to N$^1$-Aryl-N$^5$-alkyldiguanides. *J. Chem. Soc.* 1948, 1630–1636.

1-[3-(4-Chlorophenoxy)propyloxy]-5-isopropylbiguanide Dihydrochloride

A mixture of 656 g (2.00 mole) of 1-[3(4-Chlorophenoxy) propyloxy-5-isopropylbiguanide and 1.0 L of EtOAc was swirled and cooled in an ice bath before 500 g of EtOAc containing 74.5 (2.04 moles) of HCl was added. After 10 minutes a second 500 g (2.04 moles) of the HCl in EtOAc was added in small portions with swirling and cooling in the ice bath. The thick precipitate was thinned with 500 mL of EtOAc. After air-drying the material was ground with a mortar and pestle, dried at 50° C., and then at a vacuum of 1 mm to give 793 g (99%) of product mp 160–165° C.

1-[3-(4-Chlorophenoxy)propyloxy]-5-isopropylbiguanide hemisuccinate

A mixture of 3.278 g (10 mmoles) of 1-[3(4-Chlorophenoxy)propyloxy-5-isopropylbiguanide and 0.594 g (5.0 mmoles) of succinic acid were dissolved in 7 mL of hot ethanol and 11 mL of water was added dropwise with heating. The solution was allowed to cool to room temperature. The precipitate was collected, washed with 4 mL of ice-cold 50% ethanol and dried at 105° C. for 2 hours to yield 3.65 g (94.3%) of product mp 149-5–150° C. $^1$H-NMR (DMSO-d$_6$) δ1.05 (d, 6H), 2.0 (m, 2H), 3.75–4.10 (m, 5H), 5.45 (br s, 2H), 6.0 (br s, 1H), 6.87.2 (m, 4H), 7.35 (s, br, 4H).

BIOLOGICAL ACTIVITY

Toxicity

Toxicity is shown as decrease in testis weight/body weight in TABLE I. The testing was conducted as described hereunder with PS-15, and several of its analogs with equivalent or better antimalarial potency.

Male CD-1 mice were fed drug treated feed for 106 days. For the first 79 days the drug level was 300 ppm and then 600 ppm for days 80–106. The animals were then sacrificed and the organs were both weighed and examined for pathology. Testis damage was found for PS-15. Unexpectedly and unlike other analogs tested PS-26 and PS-33 showed no decrease in testis weight/body weight and minimal to no observable pathology.

TABLE I

| | Mean values for testes of 8-mice groups | | | |
|---|---|---|---|---|
| Compound | Left, % body wt | P Value | Right, % body wt. | P Value |
| None (control) | 0.30 | | 0.31 | |
| PS-15 | 0.21 | 0.01 | 0.22 | 0.01 |
| PS-26 | 0.29 | 0.87 | 0.32 | 0.79 |
| PS-33 | 0.27 | 0.30 | 0.36 | 0.77 |
| 2,4-Dichloro | 0.19 | 0.00 | 0.20 | 0.00 |
| 3,4-Difluoro | 0.21 | 0.00 | 0.23 | 0.00 |

In Vivo Activity

In vivo[1] antimalarial activity was tested in male or female Charles River CD-1 mice that were 4–5 weeks old and weighed 20–25 g. They were housed in groups of 3 or 4 in standard plastic cages with wire tops, bed-o-cob® bedding, 12 hr/day of light, and maintained at 75° F. They were fed a standard Ralston Purina mouse chow and the cages and water bottles were changed twice a week. Test compounds were ground in a mortar and pestle and diluted with enough vehicle to give a volume of 10 mL/kg of mouse weight. The oral doses were prepared in 0.5% hydroxyethylcellulose-0.1% Tween-80. The amount of drug was calculated on the free base weight. The mice were infected intraperitoneally on day 0 with $5 \times 10^4$ erythrocytes parasitized with *Plasmodium berghei* (KBG-173 strain) from a donor mouse having a parasitemia between 5–10%. On days 3,4,5 the test compounds were administered bid, spaced 6 h apart, to mice. Smears were made from tail blood on day +6 and twice a week thereafter. The smears were stained with Geimsa and examined microscopically. Parasitemias are reported as the % of the red blood cells that are infected. On day 6 the (suppression of) parasitemias of treated animals may be compared to the parasitemias of infected non-treated controls, but these infected non-treated controls die on days 7–12. Activity was also measured by survival. Full activity is defined as all animals living at day 31. Partial activity is defined as days of increased survival versus the infected non-treated controls. Results of the testing is shown in TABLE II. ≠This in vivo model is a modification of the Thompson Test. For further description see Ager, A. L., Jr. Rodent Malaria Models. In Handbook of Experimental Pharmacology: Antimalarial Drugs. 1. 68/1; Peters, W., Richards, W. H. G., Eds.: Springer-Verlag: Berlin, 1984, pp. 231 33.

TABLE II

| Compound | Dose in mg/kg | 6 day Parasetemia (Values in parentheses for nontreated controls) | Average days Survival (Values in parentheses for nontreated controls) |
|---|---|---|---|
| PS-15 | 64 | 0(39) | >31*(9.0) |
| | 32 | 0.01(39) | 21.8(9.0) |
| | 16 | 1.8(39) | 14.1(9.0) |
| | 64 | 0(37) | >24.7(8.0) |
| | 32 | 0(37) | 15.9(8.0) |
| | 16 | 2.7(37) | 15.1(8.0) |

TABLE II-continued

| Compound | Dose in mg/kg | 6 day Parasetemia (Values in parentheses for nontreated controls) | Average days Survival (Values in parentheses for nontreated controls) |
|---|---|---|---|
| | 32 | 0.006(37) | 17.8(9.2) |
| | 16 | 1.94(37) | 14.6(9.2) |
| | 32 | 0(35) | 12.8(9.8) |
| | 16 | 1.1(35) | 13.6(9.0) |
| PS-33 | 64 | 0(39) | >31*(9.0) |
| | 32 | 0.01(39) | 21.8(9.0) |
| | 16 | 1.8(39) | 14.1(9.0) |
| | 64 | 0(37) | >24.7(8.0) |
| | 32 | 0(37) | 15.9(8.0) |
| | 16 | 2.7(37) | 15.1(8.0) |
| | 32 | 0.006(37) | 17.8(9.2) |
| | 16 | 1.94(37) | 14.6(9.2) |
| | 32 | 0(35) | 12.8(9.8) |
| | 16 | 1.1(35) | 13.6(9.8) |
| PS-26 | 64 | 0(37) | >31*(8) |
| | 32 | 0(37) | >29.3(8) |
| | 16 | 0(37) | 15.7(8) |
| | 32 | 0(37) | >31(9.2) |
| | 16 | 0.006(37) | 16.6(9.2) |
| | 32 | 0(35) | >31(9.8) |
| | 16 | 0(35) | 16.0(9.8) |

*>31 means all animals survived at the end of the experiment. A > sign in from of a number >31 means some of the animals survived the 31 day experiment.

Mice were infected with *Plasmodium berghei* on day 0 and the drugs were mixed in HEC Tween and given orally bid on days 3,4, and 5 post infection. Blood films were taken hereafter until day 30. Results are shown in TABLE III.

TABLE III

Comparison of the Antimaterial Activity of Analogs of PS-15 in Mice Infected with *Plasmodium berghei*.

| DRUG | MK/KG/DAY | AVG. DAY OF DEATH | CD |
|---|---|---|---|
| Infection Control | 0 | 08.0 | — |
| PS-15 | 64 | 17.0 | |
| | 32 | 15.7 | −50 |
| | 16 | 15.1 | |
| PS-26 | 64 | — | |
| | 32 | 15.5 | −25 |
| | 16 | 16.6 | |
| PS-33 | 64 | 29.0 | |
| | 32 | 19.5 | −30 |
| | 16 | 16.0 | |

As shown, the compounds of the present invention possess potent antimalarial activity and greatly reduced toxicity when administered to mammalian subjects.

What is claimed is:

1. A method of protecting subjects from infections caused by an organism selected from the group consisting of: Plasmodium sp., Mycobacterium sp., and *Pneumocystis carinii* which comprises administering to a subject liable to infection by exposure to such organism, a composition comprising a prophylactically effective amount of a compound of the formula

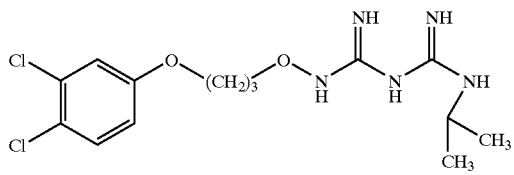

or a pharmaceutically acceptable salt thereof, wherein said composition does not cause testicular atrophy in male subjects.

2. A method of reducing the level of infection in a subject suffering therefrom caused by an organism selected from the group consisting of: Plasmodium sp., Mycobacterium sp., and *Pneumocystis carinii* which comprises administering to an infected subject, a composition comprising an infection reductively effective amount of a compound of the formula

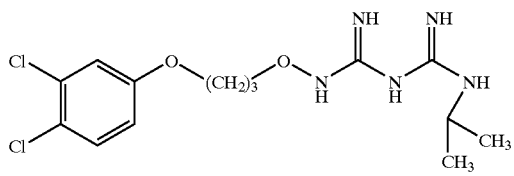

or a pharmaceutically acceptable salt thereof;

wherein said composition does not cause testicular atrophy in male subjects.

3. A method of protecting subjects from infections caused by an organism selected from the group consisting of: Plasmodium sp., Mycobacterium sp., and *Pneumocystis carinii* which comprises administering to a subject liable to infection by exposure to such organism, a composition comprising a prophylactically effective amount of a compound of the formula:

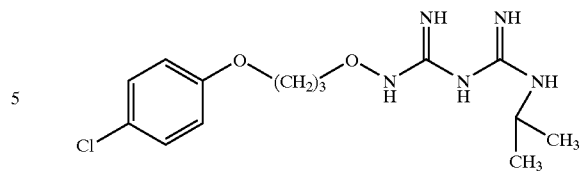

or a pharmaceutically acceptable salt thereof, wherein said composition does not cause testicular atrophy in male subjects.

4. A method of reducing the level of infection in a subject suffering therefrom caused by an organism selected from the group consisting of: Plasmodium sp., Mycobacterium sp., and *Pneumocystis carinii* which comprises administering to an infected subject, a composition comprising an infection reductively effective amount of a compound of the formula:

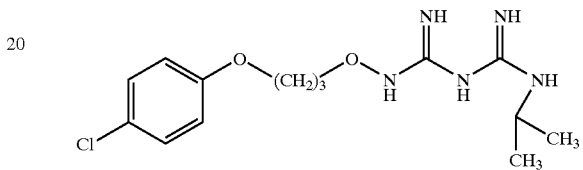

or a pharmaceutically acceptable salt thereof, wherein said composition does not cause testicular atrophy in male subjects.

5. The method of claim 1, wherein said organism is selected from the group consisting of *P. falciparum, M. avium* complex, *M. tuberculosis* and *M. kanasii*.

6. The method of claim 2, wherein said organism is selected from the group consisting of *P. falciparum, M. avium* complex, *M. tuberculosis* and *M. kanasii*.

7. The method of claim 3, wherein said organism is selected from the group consisting of *P. falciparum, M. avium* complex, *M. tuberculosis* and *M. kanasii*.

8. The method of claim 4, wherein said organism is selected from the group consisting of *P. falciparum, M. avium* complex, *M. tuberculosis* and *M. kanasii*.

\* \* \* \* \*

UNITED STATES PATENT AND TRADEMARK OFFICE
CERTIFICATE OF CORRECTION

PATENT NO. : 6,551,614 B2
DATED : April 22, 2003
INVENTOR(S) : Jacobus et al.

It is certified that error appears in the above-identified patent and that said Letters Patent is hereby corrected as shown below:

Column 2,
Line 49, please delete "PS 15 (both instances)" and insert therefor -- PS-15 --.

Column 3,
Line 43, please delete "PS 15" and insert therefor -- PS-15 --.

Column 4,
Line 1, please label the compound -- PS-26 --.

Column 5,
Between lines 45-55, compound No. 4 should be corrected as shown below:

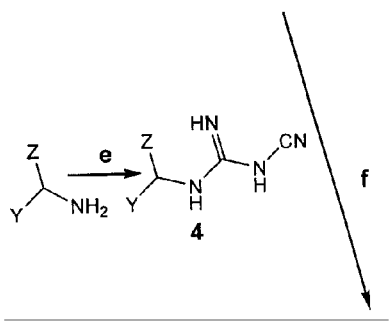

Column 6,
Line 10, delete "3,4dichlorophenol" and insert therefor -- 3,4-dichlorophenol --.
Line 65, delete "mixutre" and insert therefor -- mixture --.
Line 66, after "at" please insert -- an --.

Column 7,
Line 40, delete "PS33" and insert therefor -- PS-33 --.
Line 59, delete "3-(4Chlorophenoxy)" and insert therefor -- 3-(4-chlorophenoxy) --.

Column 8,
Line 4, delete "3-(4chlorophenoxy)" and insert therefor -- 3-(4-chlorophenoxy) --.
Line 31, delete "≠".

Column 9,
Line 53, delete "231 33" and insert therefor -- 231-33 --.

UNITED STATES PATENT AND TRADEMARK OFFICE
CERTIFICATE OF CORRECTION

PATENT NO. : 6,551,614 B2
DATED : April 22, 2003
INVENTOR(S) : Jacobus et al.

It is certified that error appears in the above-identified patent and that said Letters Patent is hereby corrected as shown below:

<u>Column 10,</u>
Line 27 (after Table II), delete "from" and insert therefor -- front --.
Line 35, delete "hereafter" and insert therefor -- on day 6 and twice weekly thereafter --.

Signed and Sealed this

Twentieth Day of July, 2004

JON W. DUDAS
*Acting Director of the United States Patent and Trademark Office*